United States Patent
Somogyi

(10) Patent No.: US 7,371,892 B2
(45) Date of Patent: May 13, 2008

(54) METHOD FOR PROCESSING β-SULPHATOETHYLSULPHONYLANILINE-2-SULPHONIC ACID

(75) Inventor: Laszlo Somogyi, Limburgerhof (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 83 days.

(21) Appl. No.: 10/589,972

(22) PCT Filed: Feb. 26, 2005

(86) PCT No.: PCT/EP2005/002054

§ 371 (c)(1), (2), (4) Date: Aug. 18, 2006

(87) PCT Pub. No.: WO2005/085190

PCT Pub. Date: Sep. 15, 2005

(65) Prior Publication Data

US 2007/0173661 A1 Jul. 26, 2007

(30) Foreign Application Priority Data

Mar. 3, 2004 (DE) ...................... 10 2004 010 950

(51) Int. Cl.
*C07C 309/00* (2006.01)
(52) U.S. Cl. ........................................................ 562/30
(58) Field of Classification Search ...................... None
See application file for complete search history.

(56) References Cited

U.S. PATENT DOCUMENTS 3,900,510 A * 8/1975 Fuchs et al. ................... 558/33

FOREIGN PATENT DOCUMENTS

| DE | 21 54 943 | 5/1973 |
|----|-----------|--------|
| DE | 25 38 722 | 3/1977 |
| DE | 25 38 723 | 3/1977 |
| EP | 0 753 509 | 1/1997 |
| WO | 96 02593  | 2/1996 |

* cited by examiner

*Primary Examiner*—Karl Puttlitz
(74) *Attorney, Agent, or Firm*—Oblon, Spivak, McClelland, Maier & Neustadt, P.C.

(57) ABSTRACT

A process for working up β-sulfatoethylsulfonylaniline-2-sulfonic acid from a solution in aqueous sulfuric acid, comprises a first step of the β-sulfatoethylsulfonylaniline-2-sulfonic acid being precipitated by addition of alkali or alkaline earth metal and/or ammonium salts, separated off and dissolved or the sulfuric acid being precipitated by addition of calcium salts and the resulting calcium sulfate being separated off if appropriate, and a second step of the resultant solution being adjusted to a pH between 1 and 5 by addition of alkali or alkaline earth metal or ammonium hydroxide, carbonate, bicarbonate and/or acetate, any calcium sulfate still present being separated off and the β-sulfatoethylsulfonylaniline-2-sulfonic acid being isolated from the solution.

6 Claims, No Drawings

METHOD FOR PROCESSING β-SULPHATOETHYLSULPHONYLANILINE-2-SULPHONIC ACID

This invention relates to a process for working up β-sulfatoethylsulfonylaniline-2-sulfonic acid from a solution in aqueous sulfuric acid.

β-Sulfatoethylsulfonylaniline-2-sulfonic acid is frequently used as a raw material for manufacturing azo dyes. Azo dye manufacture requires that this raw material be very pure. A commonly employed process for preparing β-sulfatoethylsulfonylaniline-2-sulfonic acid is known from DE-A 2 538 723. According to this reference, the corresponding β-sulfatoethylsulfonylaniline-2,6-disulfonic acid, which is obtainable from β-sulfatoethylsulfonylaniline by treatment with oleum, is treated in typically 30% to 96% sulfuric acid at temperatures of generally 80 to 140° C. One sulfonic acid moiety is detached in the course of this treatment.

fonylaniline-2-sulfonic acid from a solution in aqueous sulfuric acid as a pure product which is stable in storage without significant losses.

We have found that this object is achieved by a process for working up β-sulfatoethylsulfonylaniline-2-sulfonic acid from a solution in aqueous sulfuric acid, which comprises
a first step of the β-sulfatoethylsulfonylaniline-2-sulfonic acid being precipitated by addition of alkali or alkaline earth metal and/or ammonium salts, separated off and dissolved in water or the sulfuric acid being precipitated by addition of calcium salts and the resulting calcium sulfate being separated off if appropriate, and
a second step of the resultant solution being adjusted to a pH between 1 and 5 by addition of alkali or alkaline earth metal or ammonium hydroxide, carbonate, bicarbonate and/or acetate, any calcium sulfate still present being separated off and the β-sulfatoethylsulfonylaniline-2-sulfonic acid being isolated from the solution.

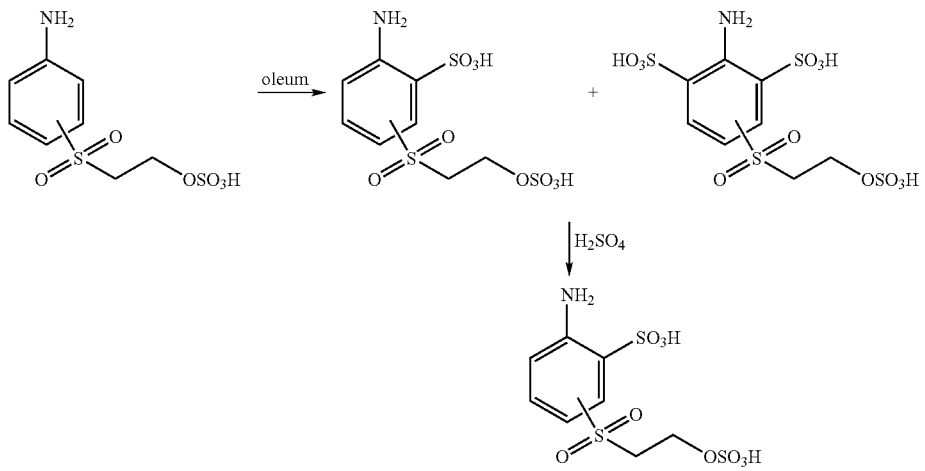

The sulfonation melt obtained is subsequently poured onto ice.

To work up β-sulfatoethylsulfonylaniline-2-sulfonic acid from this aqueous solution of sulfuric acid, the initial step is to neutralize excess sulfuric acid with alkali or alkaline earth metal hydroxides or carbonates. The sulfatoethylsulfonylaniline-2-sulfonic acid is isolated from this neutral solution by salting out with alkali metal halides or by spray drying. In Example 7, the bulk of the excess sulfuric acid is blunted with calcium carbonate and the remainder is neutralized with sodium carbonate to pH 6. However, product purity is in need of improvement with this procedure.

There has been no shortage of attempts at improving the workup process. For instance, EP-A 753 509 discloses that β-sulfatoethylsulfonylaniline-2,6-disulfonic acid can be precipitated directly from the aqueous sulfuric acid solution by addition of potassium chloride. However, this process gives a product which is not stable in storage and thus has only limited usefulness for manufacturing high-value reactive azo dyes. The exemplified recrystallization of the precipitated product further leads to not inconsiderable losses of product of value and hence is uneconomical.

It is an object of the present invention to provide a technically simple process for preparing β-sulfatoethylsul- The present invention further provides the β-sulfatoethylsulfonylaniline-2-sulfonic acid.

β-Sulfatoethylsulfonylaniline-2-sulfonic acid as used herein comprehends 5-β-sulfatoethylsulfonylaniline-2-sulfonic acid and especially 4-β-sulfatoethylsulfonylaniline-2-sulfonic acid, not only the free acid but also their salt forms such as mono- or dialkali metal, mono- or diammonium or alkaline earth metal salts with identical or different counterions.

The process of the present invention starts with an aqueous sulfuric acid solution of β-sulfatoethylsulfonylaniline-2-sulfonic acid having a concentration of generally 1% to 30% by weight, often 1% to 20% by weight and especially 5% to 20% by weight of β-sulfatoethylsulfonylaniline-2-sulfonic acid and typically 1% to 80% and often 5% to 50% by weight of sulfuric acid. Such solutions are obtainable for example by sulfonation of β-sulfatoethylsulfonylaniline or by desulfonation of β-sulfatoethylsulfonylaniline-2,6-disulfonic acid.

The first step serves to separate the β-sulfatoethylsulfonylaniline-2-sulfonic acid from the sulfuric acid.

Useful precipitants for β-sulfatoethylsulfonylaniline-2-sulfonic acid include alkaline earth metal, alkali metal and ammonium salts or mixtures thereof, preferably sodium, potassium and/or ammonium salts, especially sodium chloride, sodium sulfate, potassium chloride, potassium sulfate or mixtures thereof. The amounts can be varied within wide limits, but are typically in the range from 1 to 10 and especially from 2 to 6 mol equivalents. Product separation is not critical in that it can be carried out with customary apparatuses such as filter presses, stirred pressure nutsches, ultrafiltration equipment or belt filters.

The subsequent dissolving of the removed product in water is likewise uncritical in that it can be carried out at room temperature, but preferably with cooling at 0 to 20° C. or most simply by introduction into typically 1 to 20 liters and often 1 to 10 liters of ice-water per mole of product.

It is likewise possible to precipitate the sulfuric acid in the first step by addition of calcium salts such as calcium carbonate and/or calcium oxide. The amounts of calcium salts used are typically such that the pH adjusts to 0-2.

The removal of the calcium sulfate is not critical; it can be carried out in the first step or in the second step after the desired pH has been set. It is customary to use apparatuses such as filter presses, stirred pressure nutsches, ultrafiltration equipment or belt filters.

This solution is adjusted to a pH of 1.5 and especially 2 to 4 in the second step by addition of alkali metal, alkaline earth metal or ammonium hydroxide, carbonate, bicarbonate, acetate or mixtures thereof, especially alkali metal carbonate or alkali metal bicarbonate, for example sodium carbonate or sodium bicarbonate.

The subsequent isolation of the β-sulfatoethylsulfonylaniline-2-sulfonic acid is not critical and can be accomplished by precipitating, evaporating or spray drying. The product can be precipitated and isolated as described above. Evaporating is generally accomplished in known vacuum drying cabinets at a temperature of 30 to 70 and especially 35 to 55° C., while the often advantageous spray drying is accomplished in customary spray drying towers.

The process has many advantages. Large amounts of by-products and waste heat are avoided and a product is obtained in high yield which is pure and has balanced performance properties.

EXAMPLES

Comparative Test 1 (EP 753 509)

To an initial charge of 437 g of 20% by weight oleum are added 142 g=0.485 mol of 4-β-sulfatoethylsulfonylaniline starting at room temperature, and the temperature rises to 50° C. The solution is subsequently heated to 115±2° C. for 3 hours. The sulfonation batch is cooled down to 70-80° C. Then 42 g of 50% by weight sulfuric acid are added dropwise while the temperature should not rise above 100° C. This is followed by ten hours heating at 95 to 100° C.

The melt is cooled down to 40-50° C. and poured onto a mixture of 700 g of ice-water while cooling from the outside. In the course of the addition, the temperature should not rise above 20° C. To the resulting clear solution are added 75 g=1.0 mol of potassium chloride. This is followed by three hours of stirring before the precipitated reaction product is filtered off with suction.

The product is purified by recrystallization, suspended in 200 ml of water, heated to 70° C. and then admixed with 500 ml of hot water at 70° C. in 100 ml portions until everything is dissolved. The mixture is cooled down to 0-50 using an ice bath, and the precipitated residue is filtered off with suction and dried. The residue weighs 93.6 g and is 79.2% by weight based on molecular weight 361 4-β-sulfatoethylsulfonylaniline-2-sulfonic acid. Yield: 41%

Example 2

To an initial charge of 437 g of 20% by weight oleum are added 142 g=0.485 mol of 4-β-sulfatoethylsulfonylaniline starting at room temperature, and the temperature rises to 50° C. The solution is subsequently heated to 115±2° C. for 3 hours.

The sulfonation batch is cooled down to 70-80° C. Then 42 g of 50% by weight sulfuric acid are added dropwise while the temperature should not rise above 100° C. This is followed by ten hours heating at 95 to 100° C.

The melt is cooled down to 40-50° C. and poured onto a mixture of 700 g of ice-water while cooling from the outside. In the course of the addition, the temperature should not rise above 20° C. To the resulting clear solution are added 33.6 g=0.45 mol of potassium chloride, followed by the addition of three times 0.833 mol (48.7 g) of sodium chloride, each addition being followed by stirring for half an hour. The precipitated product is filtered off with suction and dissolved in 1200 ml of water at 15° C. The pH of the solution is adjusted to 3.0 with sodium carbonate added a little at a time. The reaction solution is concentrated to dryness under reduced pressure at 50° C. The residue weighs 412 g and is 38% by weight based on molecular weight 361 4-β-sulfatoethylsulfonylaniline-2-sulfonic acid. Yield: 87%

Example 3

4 mol (1171 g) of 4-β-sulfatoethylsulfonylaniline (96% by weight pure) are introduced into 2100 g of 96% by weight sulfuric acid, and the temperature rises to 35° C. This is followed by the addition of 1660 g of oleum 65%, and the temperature rises to 80° C. The mixture is heated to 115° C. and stirred at 115° C. for 3 hours. After cooling to 65° C., 175 g of ice are added, and the temperature rises to 90° C. The reaction mixture is heated to 95° C. and stirred at 95° C. for 10 hours. 5800 g of ice are introduced as an initial charge and the reaction mixture, which is cooled to room temperature, is added with ice-bath cooling such that the temperature does not rise above 20° C. This is followed by the addition of three times 5.128 mol (300 g) of sodium chloride, each addition being followed by an hour of stirring. The precipitated product is filtered off with suction and dissolved in ice-water (1538 g of ice; 7600 ml of water) at 12° C. The pH of the solution is adjusted to 3.0 with sodium carbonate added a little at a time. The temperature rises to 24° C. in the process. The solution is stirred at room temperature overnight and spray dried the next day. The residue weighs 2155 g and is 47% by weight based on molecular weight 361 4-β-sulfatoethylsulfonylaniline-2-sulfonic acid. Yield: 70%

Example 4

4 mol (1171 g) of 4-β-sulfatoethylsulfonylaniline (96% by weight pure) are introduced into 2100 g of 96% by weight sulfuric acid, and the temperature rises to 35° C. This is followed by the addition of 1660 g of oleum 65%, and the temperature rises to 80° C. The mixture is heated to 115° C. and stirred at 115° C. for 3 hours. After cooling to 65° C., 175 g of ice are added, and the temperature rises to 90° C. The reaction mixture is heated to 95° C. and stirred at 95° C. for 10 hours. 5800 g of ice are introduced as an initial charge and the reaction mixture, which is cooled to room temperature, is added with ice-bath cooling such that the temperature does not rise above 20° C. This is followed by the addition of three times 5.128 mol (300 g) of sodium chloride, each addition being followed by an hour of stirring. The precipitated product is filtered off with suction and dissolved in ice-water (1538 g of ice; 7600 ml of water) at 12° C. The pH of the solution is adjusted to 3.0 with sodium carbonate added a little at a time. The temperature rises to 22° C. in the process. The solution is stirred at room temperature over the weekend and is subsequently admixed with 1500 g of NaCl, which causes the product to salt out. After filtration with suction and drying, the residue weighs 2094.8 g and is 52.5% by weight based on molecular weight 361 4-β-sulfatoethylsulfonylaniline-2-sulfonic acid. Yield: 76%

Example 5

To a mixture of 1 mol (361 g) of 4-β-sulfatoethylsulfonylaniline-2-sulfonic acid, 542 g of sulfuric acid and 386 g of water are added 2 mol (150 g) of KCl in three portions, the addition of each portion being followed by an hour of stirring. The 4-β-sulfatoethylsulfonylaniline-2-sulfonic acid precipitates as the dipotassium salt in the process. The precipitated product is filtered off with suction and suspended in 2600 g of ice-water at 15° C. The pH of the mixture is adjusted to 5 by gradual addition of 10% by weight NaOH solution, and the temperature rises to 25° C. The solution is subsequently ultrafiltered and the product is isolated by spray drying.

Example 6

To a mixture of 1 mol (361 g) of 4-β-sulfatoethylsulfonylaniline-2-sulfonic acid, 1125 g of sulfuric acid and 3014 g of water are added 9 mol (531 g) of NaCl in three portions, the addition of each portion being followed by an hour of stirring. The 4-β-sulfatoethylsulfonylaniline-2-sulfonic acid precipitates as the disodium salt in the process. The precipitated product is filtered off with suction and suspended in 3300 g of ice-water at 12° C. The pH of the mixture is adjusted to 4 by gradual addition of 10% by weight NaOH solution, and the temperature rises to 23° C. The solution is subsequently evaporated to dryness.

Example 7

To a mixture of 2 mol (722 g) of 4-β-sulfatoethylsulfonylaniline-2-sulfonic acid, 10 100 g of sulfuric acid and 3600 g of water are added 5 mol (710 g) of $Na_2SO_4$ in three portions, the addition of each portion being followed by an hour of stirring. The 4-β-sulfatoethylsulfonylaniline-2-sulfonic acid precipitates as the disodium salt in the process. The precipitated product is filtered off with suction and suspended in 18 000 g of ice-water at 12° C. The pH of the mixture is adjusted to 3 by gradual addition of $K_2CO_3$, and the temperature rises to 25° C. The solution is subsequently spray dried.

Example 8

To a mixture of 1 mol (361 g) of 4-β-sulfatoethylsulfonylaniline-2-sulfonic acid, 988 g of sulfuric acid and 1250 g of water are added 4 mol (696 g) of $K_2SO_4$ in three portions, the addition of each portion being followed by an hour of stirring. The 4-β-sulfatoethylsulfonylaniline-2-sulfonic acid precipitates as the dipotassium salt in the process. The precipitated product is filtered off with suction and suspended in 18 000 g of ice-water at 8° C. The pH of the mixture is adjusted to 2 by gradual addition of $KHCO_3$, and the temperature rises to 15° C. The product is subsequently salted out by addition of 950 g of KCl, filtered off with suction and dried.

Example 9

To a mixture of 1 mol (361 g) of 4-β-sulfatoethylsulfonylaniline-2-sulfonic acid, 1080 g of sulfuric acid and 809 g of water are added 6 mol (354 g) of NaCl in three portions, the addition of each portion being followed by an hour of stirring. The 4-β-sulfatoethylsulfonylaniline-2-sulfonic acid precipitates as the disodium salt in the process. The precipitated product is filtered off with suction and suspended in 4200 g of ice-water at 14° C. The pH of the mixture is adjusted to 1 by gradual addition of $NaHCO_3$, and the temperature rises to 22° C. The product is subsequently salted out by addition of 882 g of NaCl, filtered off with suction and dried.

Example 10

To a mixture of 1 mol (361 g) of 4-β-sulfatoethylsulfonylaniline-2-sulfonic acid, 1580 g of sulfuric acid and 5260 g of water are added 1 mol (174 g) of $K_2SO_4$ and 4 mol (568 g) of $Na_2SO_4$, each addition being followed by an hour of stirring. The 4-β-sulfatoethylsulfonylaniline-2-sulfonic acid precipitates in the process. The precipitated product is filtered off with suction and suspended in 4200 g of ice-water at 15° C. The pH of the mixture is adjusted to 3 by gradual addition of sodium acetate, and the temperature rises to 25° C. The solution is subsequently spray dried.

Example 11

To a mixture of 1 mol (361 g) of 4-β-sulfatoethylsulfonylaniline-2-sulfonic acid, 864 g of sulfuric acid and 6000 g of water are added 650 g of $CaCO_3$ followed by addition of sodium carbonate until the pH is 3. The temperature is held below 20° C. The precipitated calcium sulfate hemihydrate is filtered off with suction and the 4-β-sulfatoethylsulfonylaniline-2-sulfonic acid is isolated as the disodium salt by spray-drying the filtrate solution.

Example 12

To a mixture of 1 mol (361 g) of 4-β-sulfatoethylsulfonylaniline-2-sulfonic acid, 900 g of sulfuric acid and 16 700 g of water are added 680 g of $CaCO_3$ followed by addition of $K_2CO_3$ until the pH is 1. The temperature is held below 60° C. The precipitated calcium sulfate hemihydrate is filtered off with suction and the 4-β-sulfatoethylsulfonylaniline-2-sulfonic acid is isolated as the dipotassium salt by spray-drying the filtrate solution.

Example 13

To a mixture of 1 mol (361 g) of 4-β-sulfatoethylsulfonylaniline-2-sulfonic acid, 860 g of sulfuric acid and 5800 g of water are added 650 g of $CaCO_3$ followed by addition of $NaHCO_3$ until the pH is 2. The temperature is held below 40° C. The precipitated calcium sulfate hemihydrate is filtered off with suction and the 4-β-sulfatoethylsulfonylaniline-2-sulfonic acid is isolated as the disodium salt by spray-drying the filtrate solution.

Example 14

To a mixture of 0.5 mol (180.5 g) of 4-β-sulfatoethylsulfonylaniline-2-sulfonic acid, 433 g of sulfuric acid and 1200 g of water are added 350 g of CaCO₃ followed by addition of KHCO₃ until the pH is 4. The temperature is held below 35° C. The precipitated calcium sulfate hemihydrate is filtered off with suction and the 4-β-sulfatoethylsulfonylaniline-2-sulfonic acid is salted out by addition of 680 g of KCl, filtered off with suction and dried.

Example 15

To a mixture of 2 mol (722 g) of 4-β-sulfatoethylsulfonylaniline-2-sulfonic acid, 1680 g of sulfuric acid and 2400 g of water are added 1300 g of CaCO₃ followed by addition of 10% by weight NaOH solution until the pH is 5. The temperature is held below 25° C. The precipitated calcium sulfate hemihydrate is filtered off with suction and the 4-β-sulfatoethylsulfonylaniline-2-sulfonic acid is salted out by addition of 1450 g of NaCl, filtered off with suction and dried.

Example 16

To a mixture of 1 mol (361 g) of 4-β-sulfatoethylsulfonylaniline-2-sulfonic acid, 871 g of sulfuric acid and 6100 g of water are added 740 g of CaCO₃. The precipitated calcium sulfate hemihydrate is filtered off with suction and the pH of the filtrate solution is raised to 3 by addition of sodium acetate. The temperature is held below 20° C. The 4-β-sulfatoethylsulfonylaniline-2-sulfonic acid is isolated as the disodium salt by spray-drying the filtrate solution.

Example 17

To a mixture of 1 mol (361 g) of 4-β-sulfatoethylsulfonylaniline-2-sulfonic acid, 885 g of sulfuric acid and 2350 g of water are added 725 g of CaCO₃. The precipitated calcium sulfate hemihydrate is filtered off with suction and the pH of the filtrate solution is raised to 4 by addition of sodium carbonate. The temperature is held below 28° C. The 4-β-sulfatoethylsulfonylaniline-2-sulfonic acid is isolated as the disodium salt by evaporating the filtrate solution.

Example 18

CaCO₃ is added at 25° C. to a mixture of 1 mol (361 g) of 4-β-sulfatoethylsulfonylaniline-2-sulfonic acid, 885 g of sulfuric acid and 2350 g of water until the pH is 3. The precipitated calcium sulfate hemihydrate is filtered off with suction and the 4-β-sulfatoethylsulfonylaniline-2-sulfonic acid is isolated as the calcium salt by spray-drying the filtrate solution.

Example 19

To a mixture of 1 mol (361 g) of 4-β-sulfatoethylsulfonylaniline-2-sulfonic acid, 988 g of sulfuric acid and 1250 g of water are added 8 mmol (428 g) of NH₄Cl in three portions, the addition of each portion being followed by an hour of stirring. The 4-β-sulfatoethylsulfonylaniline-2-sulfonic acid precipitates as the diammonium salt in the process. The precipitated product is filtered off with suction and suspended in 3600 g of ice-water at 8° C. The pH of the mixture is adjusted to 2 by gradual addition of (NH₄)₂CO₃, and the temperature rises to 15° C. The solution is subsequently ultrafiltered and the product is isolated by spray drying.

The invention claimed is:

1. A process for working up 4-β-sulfatoethylsulfonylaniline-2-sulfonic acid from a solution in aqueous sulfuric acid, which comprises
   a first step of either precipitating the 4-β-sulfatoethylsulfonylaniline-2-sulfonic acid by addition of alkali metal, alkaline earth metal and/or ammonium salts, separating the precipitate from the solution and dissolving said precipitate in water, or precipitating the sulfuric acid by addition of calcium salts with the resulting calcium sulfate precipitate optionally being separated off, and
   a second step of adjusting the resultant solution to a pH between 1 and 5 by addition of alkali metal, alkaline earth metal or ammonium hydroxide, carbonate, bicarbonate and/or acetate, with any calcium sulfate precipitate still present being separated off, and thereafter isolating the 4-β-sulfatoethylsulfonylaniline-2-sulfonic acid from the solution.

2. The process according to claim 1 wherein the 4-β-sulfatoethylsulfonylaniline-2-sulfonic acid is precipitated by the addition of 1 to 10 mol equivalents of sodium, potassium and/or ammonium salts in the first step.

3. The process according to claim 1 wherein the salts in the first step are selected from the group consisting of sodium chloride, sodium sulfate, potassium chloride and potassium sulfate.

4. The process according to claim 1 wherein the 4-β-sulfatoethylsulfonylaniline-2-sulfonic acid is isolated in the second step by precipitating with sodium, potassium and/or ammonium salts or by spray drying.

5. The process according to claim 4 wherein the 4-β-sulfatoethylsulfonylaniline-2-sulfonic acid is isolated in the second step by precipitating with 1 to 10 mol equivalents of said salts.

6. The process according to claim 4 wherein the salts are selected from the group consisting of sodium chloride and the sodium sulfate as the sodium salts and potassium chloride and potassium sulfate as the potassium salts.

* * * * *